(12) United States Patent
Fischer et al.

(10) Patent No.: US 6,610,034 B1
(45) Date of Patent: Aug. 26, 2003

(54) THREAD LOCKING STRUCTURE

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/489,173

(22) Filed: Jan. 21, 2000

(51) Int. Cl.$^7$ ................................................ A61M 5/31
(52) U.S. Cl. ...................................... 604/241; 604/235
(58) Field of Search ................................ 604/240, 241, 604/235, 533–537; 433/88–90; 411/271, 273, 383, 384; 366/322, 324, 329.1

(56) References Cited

U.S. PATENT DOCUMENTS

| | | | |
|---|---|---|---|
| 2,423,762 A | * 7/1947 | Everett | 604/241 |
| 3,729,031 A | 4/1973 | Baldwin | 141/2 |
| 3,934,831 A | * 1/1976 | Bruggisser et al. | 242/477.3 |
| 4,046,145 A | 9/1977 | Choksi et al. | 128/215 |
| 4,743,229 A | 5/1988 | Chu | 604/82 |
| 4,782,681 A | * 11/1988 | Kawashima | 72/88 |
| 4,846,614 A | * 7/1989 | Steinbock | 411/307 |
| 5,643,206 A | 7/1997 | Fischer | 604/82 |

OTHER PUBLICATIONS

"Conical Fittings with a 6% (Luer) Taper for Syringes, Needles and Certain Other Medical Equipment—Part 1: General Requirements" *International Standard*, ISO 594/1, First Edition Jun. 15, 1986.

"Conical Fittings with a 6% (Luer) Taper for Syringes, Needles and Certain Other Medical Equipment—Parts 2: Lock Fittings" *International Standard*, ISO 594/2, First Edition May 1, 1991.

* cited by examiner

*Primary Examiner*—Manuel Mendez
(74) *Attorney, Agent, or Firm*—Workman, Nydegger & Seeley

(57) ABSTRACT

A syringe system includes a first syringe having a barrel with a tubular tip formed at the end thereof. The tubular tip has an exterior surface with a pair of spaced apart first threads outwardly projecting therefrom so as to at least partially encircle the tubular tip. A second syringe has a barrel with a collar formed at the end thereof. The collar has an interior surface with engagement threads projecting therefrom. The collar is configured to receive the tip of the first syringe such that the first threads can selectively threadedly couple with the engagement threads. A pair of second threads project from the exterior surface of the tubular tip so as to at least partial encircle the tubular tip, the second threads being longitudinally spaced apart from the first threads. The second threads can be rotated, shifted, or otherwise shaped into a variety of different configurations so as to aggressively engage the engagement threads in frictional bias when the first syringe is coupled to the second syringe. In an alternative embodiment, the second threads can be replaced by a ridge which is contigured to frictionally engage with the engagement threads.

23 Claims, 8 Drawing Sheets

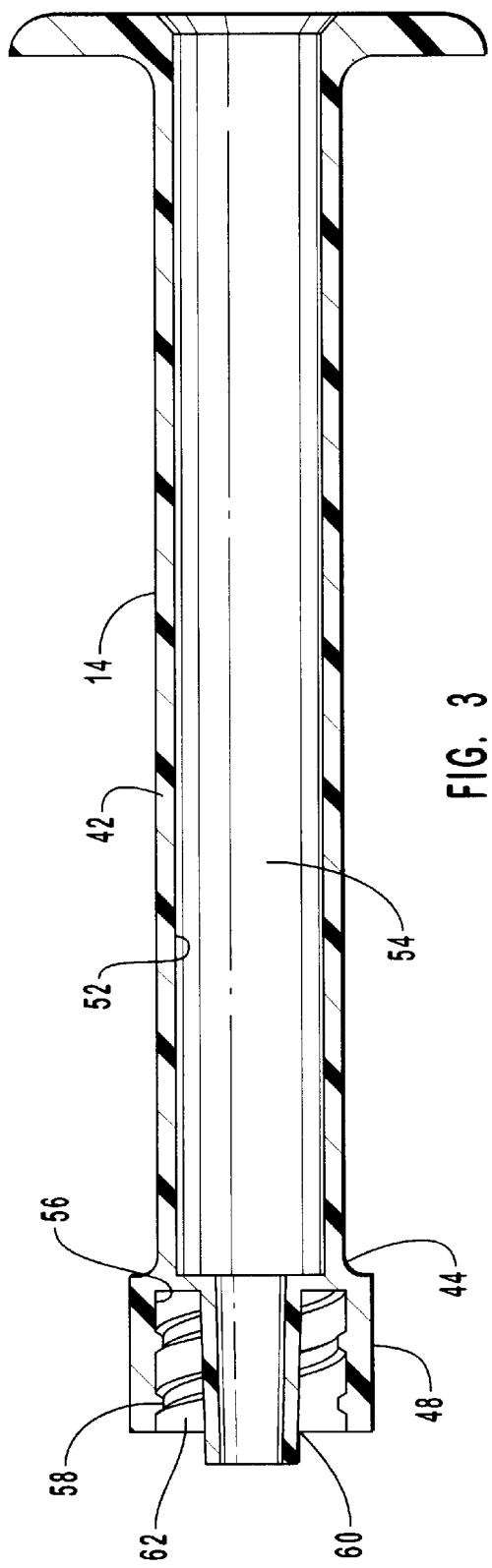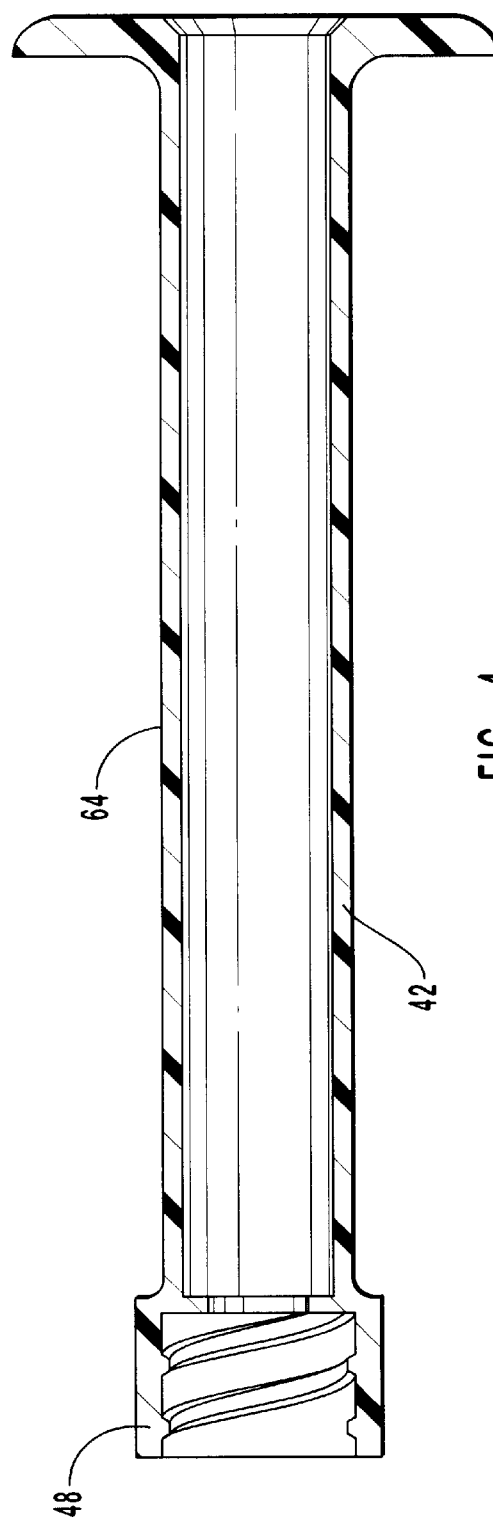

THREAD LOCKING STRUCTURE

BACKGROUND OF THE INVENTION

1. The Field of the Invention

The present invention relates to structure for coupling syringes and other dispensing or mixing apparatus together and, more specifically, structures for threadedly coupling together syringes or other related types of devices in a secure liquid tight engagement.

2. The Prior State of the Art

Occasionally it is necessary to mix two components together before dispensing the resulting composition. For example, various adhesives and dental compositions comprise two discrete components which are independently stable but when combined interact to set in a cementitious manner. One approach to combining the discrete components is simply to dispense each of the discrete components into a third compartment where they are mixed and subsequently dispensed. In an alternative approach, the individual components are each retained in a respective syringe. The dispensing ends of the syringes are coupled together and the discrete components are passed back and forth between the syringes by advancing and retracting the corresponding plunger. The components are passed back and forth until the components are fully mixed. The mixed composition is then loaded into one of the syringes for subsequent dispensing while the later syringe is simply discarded.

A similar approach is also used in transferring material between syringes. That is, bulk quantities of materials, such as many dental compositions, are often stored in relatively large syringes. In order to mix measured amounts of the stored materials or to more easily apply the materials, a large bulk syringe is coupled with a smaller syringe such that a measured amount of the stored material can be transferred to the smaller syringe.

One approach to coupling two syringes together has been the use of discrete connectors which either press fit or threadedly engage with the nozzles of the syringes. Although such connectors are useful in many situations, such connectors often fail when it is necessary to transfer highly viscous materials between syringes, In such situations, the syringes will often separate from the connectors under the force applied to the material by the plunger. This problem is further exacerbated where the material being transferred is highly lubricious, thereby making the coupling between the syringe and the connector slippery.

It is further noted that the use of a discrete connector to couple two syringes together is undesirable in that the connector is an added expense to the system. Furthermore, such connectors are time consuming in use in that they require a separate connection to each of the syringes.

SUMMARY OF THE INVENTION

Accordingly, it is an object of the present invention to provide structure for coupling two syringes together such that material can be transferred therebetween.

Another object of the present invention is to provide structure as above which enables the syringes to be tightly secured together in a liquid tight fashion such that highly viscous and lubricious materials can be transferred between the syringes without unwanted separation or leaking of the syringes.

Finally, another object of the present invention is to provide structure as above which in one embodiment enables coupling of the two syringes without the use of a separate and discrete connector.

To achieve the foregoing objects and in accordance with the invention as described and claimed herein, a syringe system is provided. The syringe system includes a first syringe having a barrel with a tubular tip formed at the end thereof. The tubular tip has an exterior surface with a pair of spaced apart first threads outwardly projecting therefrom so as to at least particularly encircle the tubular tip. The first threads bound a first thread groove extending therebetween.

The syringe system also includes a second syringe having a barrel with a collar formed at the end thereof. The collar has an interior surface with engagement threads projecting therefrom. The collar is configured to receive the tip of the first syringe barrel such that the first threads can be selectively threadedly coupled with the engagement threads, thereby coupling the two syringes together.

The present invention also includes means mounted on the exterior surface of the tubular tip of the first syringe barrel at a location longitudinally spaced apart from the first threads for frictionally engaging the second syringe when the first syringe is threadedly coupled to the second syringe. In one embodiment, the means for frictionally engaging the second syringe comprises a pair of spaced apart second threads projecting from the exterior surface of the barrel so as to at least partially encircle the tubular barrel, the second threads being longitudinally spaced apart from the first threads.

The second threads can be substantially identical to the first threads or they can have a variety of alternative configurations. For example, the second threads can have a larger diameter and/or thickness than the first threads so as to more aggressively engage the second syringe. Furthermore, the second threads can be shifted to be slightly off-set from the first threads, rotated to a different pitch than the first threads, or sized to bound constricting or narrow grooves such that as the engagement threads couple with the second threads, the second threads aggressively bind with the engagement threads under frictional bias.

In yet another alternative embodiment of the means for frictionally engaging, the second threads can be replaced with a ridge. The ridge can either encircle the tubular tip or simply be aligned with the groove of the first threads. The ridge is configured to bias in frictional engagement with the engagement threads so as to securely lock the two syringes together in a liquid-tight fashion. The above second threads and ridge can be configured for a single or repeated coupling between the syringes.

By use of the above second threads, ridge, and other corresponding embodiments as disclosed herein, a tight friction coupling is provided between the two syringes. As a result of the secure nature of this coupling, highly viscous and lubricious materials can be repeatedly passed back and forth between the syringes without risk of accidental leaking or uncoupling of the syringes.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3 is a cross sectional side view of the second syringe shown in FIG. 1;

FIG. 4 is a cross sectional side view of an alternative embodiment of the second syringe shown in FIG. 1;

DETAILED DESCRIPTION OF PREFERRED EMBODIMENTS

Figure 1:
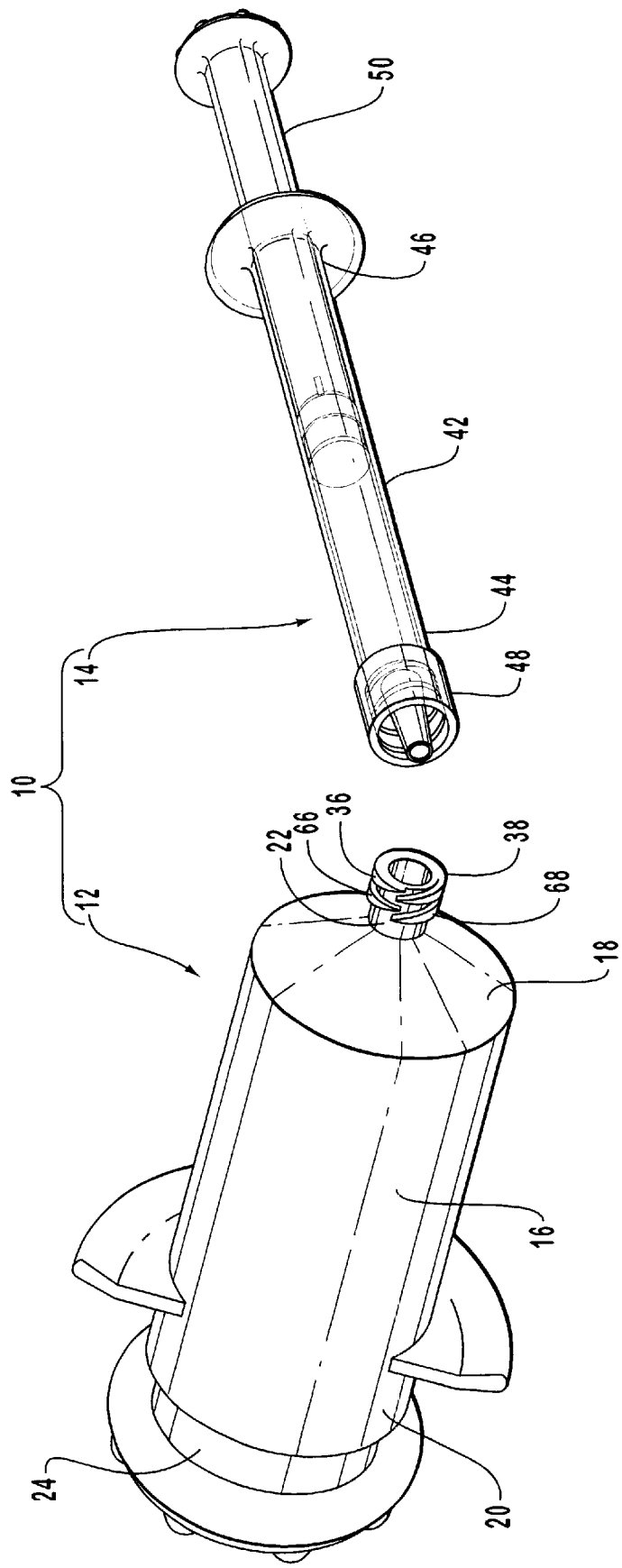
FIG. 1 is a perspective view of a first syringe and a second syringe configured for selective coupling together.
Figure 2:
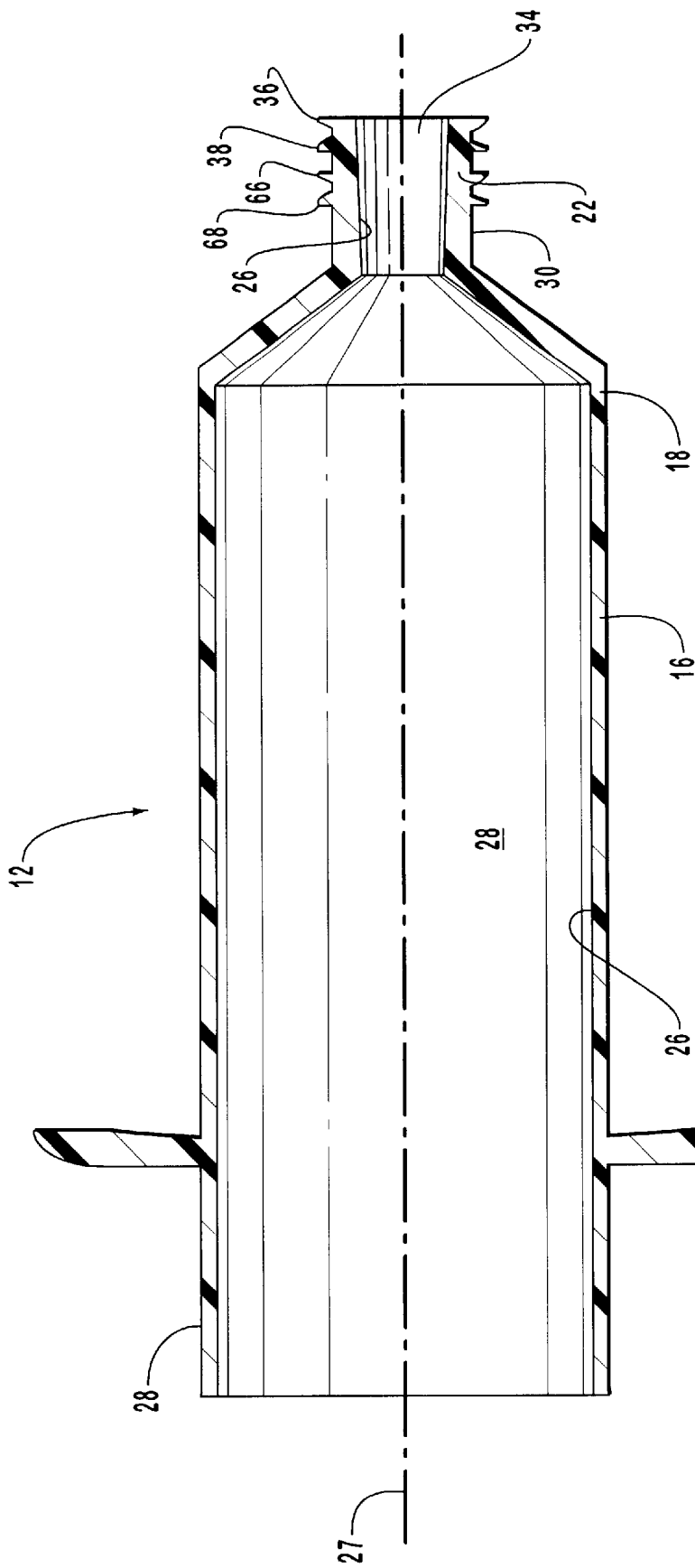
FIG. 2 is a cross sectional side view the first syringe shown in FIG. 1.

Depicted in FIG. 1 is one embodiment of a syringe system 10 incorporating features of the present invention. Syringe system 10 includes a first syringe 12 and a second syringe 14 which are designed to be coupled together so as to pass one or more components therebetween. First syringe 12 includes a barrel 16 having a first end 18 and an opposing second end 20. Projecting from first end 18 is a tubular tip 22. Slideably disposed within second end 20 of barrel 16 is a plunger 24. As depicted in FIG. 2, barrel 16 has an interior surface 26 bounding a chamber 28. Chamber 28 is configured to slidably receive plunger 24 (FIG. 1) and to hold a component (not shown) for mixing and/or dispensing.

Tip 22 of first syringe 12 is shown having an exterior surface 30 and an opposing interior surface 26. Interior surface 26 bounds a channel 34 in fluid communication with chamber 28. As discussed below in greater detail, in one embodiment, interior surface 26 is tapered into a frustoconical configuration. A central longitudinal axis 27 extends through channel 34 and chamber 28. In the embodiment depicted, tubular tip 22 has a smaller outer diameter than barrel 16. In alternative embodiments, however, tip 22 may have the same or other varied diameter relative to barrel 16. In such embodiments, tip 22 merely defines one end of barrel 16.

As depicted in FIGS. 1 and 2, outwardly projecting from exterior surface 30 at the end of tip 22 are a pair of spaced apart first threads 36 and 38. In one embodiment, first threads 36 and 38 comprise a pair of right hand threads. In the embodiment depicted, each of first threads 36 and 38 only partially encircle tip 22. In alternative embodiments, one or both of first threads 36 and 38 may completely encircle tip 22 one or more times.

Figure 6:
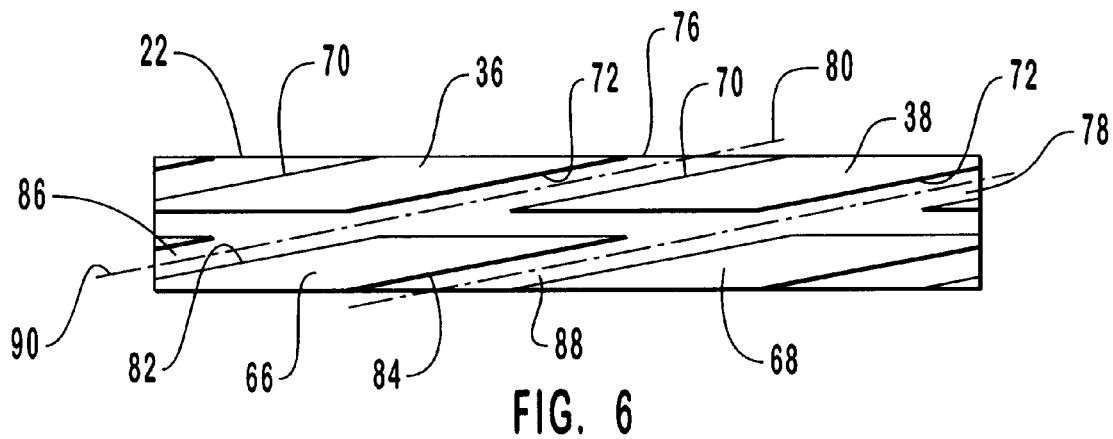
FIG. 6 is a top plan view of a schematic representation of the tip of the barrel of the first syringe shown in FIG. 1 unrolled into a flat plane, the tip of the barrel having a pair of first threads and a pair of second threads upwardly projecting therefrom.
Figure 7:
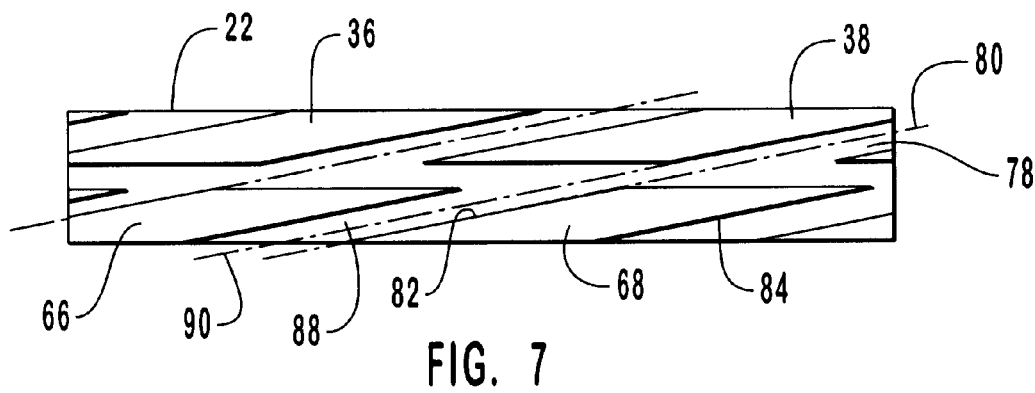
FIG. 7 is a top plan view of an alternative embodiment of the thread assembly shown in FIG. 6 with the second threads being displaced relative to the first threads.

Depicted in FIG. 6 is a top plan view of a schematic layout wherein tubular tip 22 of first syringe 12 has been unrolled into a flat configuration with the first threads 36, 38 projecting upwardly therefrom. This view is provided so as to enable a simultaneous view of both of the threads and to more clearly define their relative positions. It is appreciated that the drawing is merely illustrative and may not be structurally or proportionally properly transposed from the circular configuration.

Figure 5:
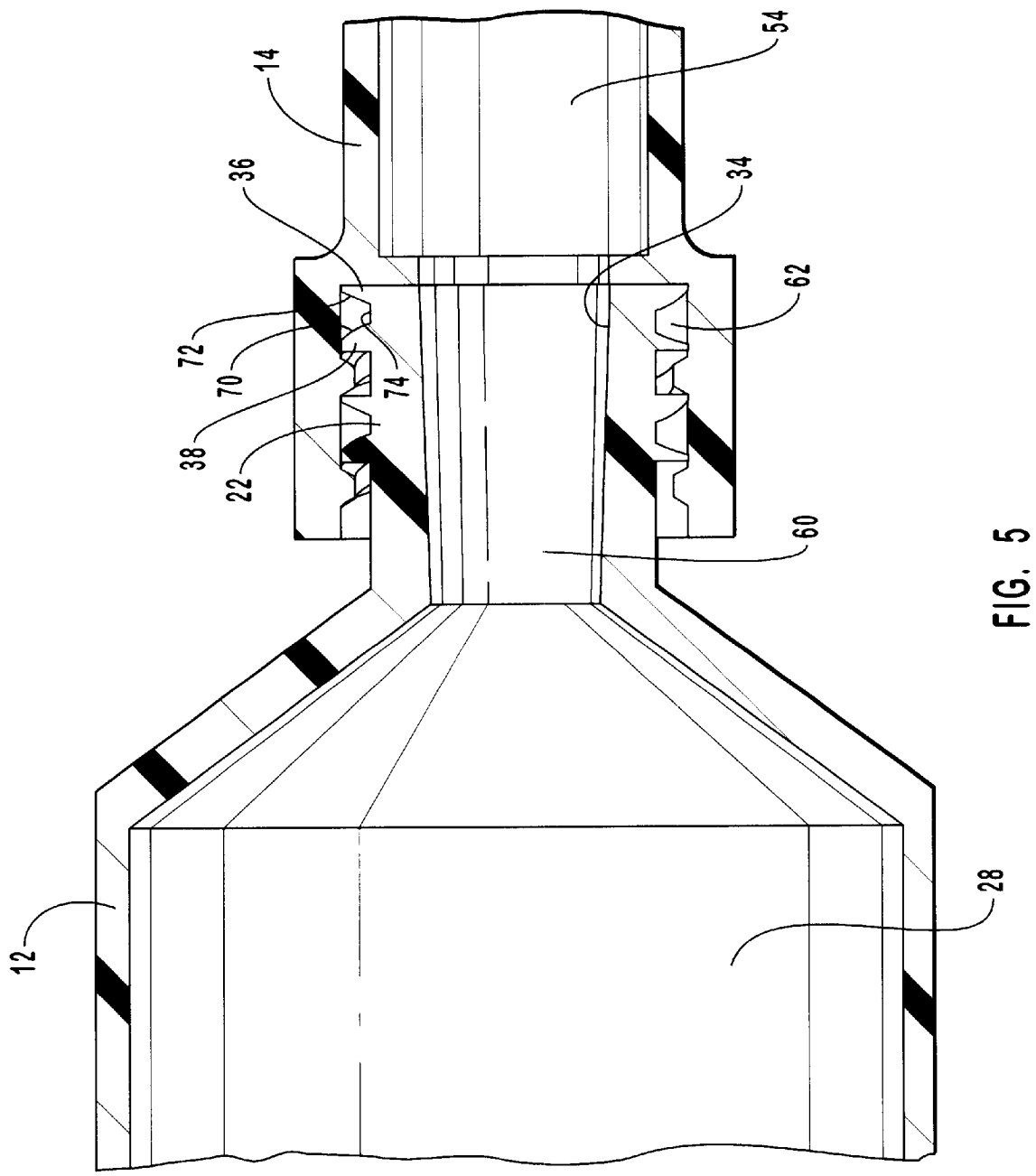
FIG. 5 is a cross section side view of the first syringe and the second syringe shown in FIG. 1 coupled together.

Depicted in FIGS. 5 and 6, each of first threads 36 and 38 has opposing side walls 70 and 72. As depicted in FIG. 5, each of the side walls 70 and 72 taper downwardly at an angle to a substantially flat floor 74. The opposing facing side walls 70 and 72 between the first threads 36, 38 bound a pair of first thread grooves 76 and 78. Depicted in FIG. 6, a central longitudinal axis 80 longitudinally extends through each first thread groove 76, 78. In one embodiment, the angle of the tapered side walls 70 and 72, the width of the first thread grooves 76 and 78, and the pitch of the first threads 36 and 38 are comparable to the corresponding dimensions of the female 6% (Luer) lock conical fitting with external thread as set forth in International Standard ISO 594-2:1991 (E) which is incorporated herein by specific reference. In alternative embodiments, first threads 36, 38 can have vertically or alternatively sloped sidewalls, a grooved floor 74, and other alternative configurations.

Returning to FIG. 1, second syringe 14 includes a barrel 42 having a first end 44 and an opposing second end 46. Slidably disposed within the second end 46 of barrel 42 is plunger 50. Depicted in FIG. 3, barrel 42 has an interior surface 52 bounding a chamber 54. Chamber 54 is configured to slidably receive plunger 50 (FIG. 1) and to hold a component (not shown) for mixing and/or dispensing. A tubular collar 48 projects from first end 44 of barrel 42. Collar 48 has an interior surface 56. Inwardly projecting from interior surface 56 are a pair of engagement threads 58. Projecting from first end 44 of barrel 42 centrally within collar 48 is a tubular lure cone 60. Lure cone 60 has a tapered configuration complementary to channel 34 of tip 22. As annular recess 62 is formed between the exterior lure cone 60 and the interior of collar 48.

As depicted in FIG. 5, first syringe 12 and second syringe 14 are configured such that tubular tip 22 can be selectively received within recess 62 and secured therein by threaded engagement between first threads 36, 38 and engagement threads 58. In this configuration, lure cone 60 is received in frictional engagement within channel 34 of tubular tip 22. In this coupled engagement, chambers 28 and 54 are in fluid communication. By selectively advancing one of plungers 24 or 50, the component within the syringe of the advancing plunger is passed into the chamber of the opposing syringe. Furthermore, by selectively advancing and retracting each of plungers 24 and 50, discrete components within each of syringes 12 and 14 can be passed back and forth between the two syringes, thereby mixing the two components.

Syringes 12 and 14 can be of any desired size or configuration and can be used with any desired types of components in any desired environment, such as medical, dental, or industrial. In one embodiment, syringes 12 and 14 are injection molded from plastic. The syringes can also be manufactured by other milling or molding processes and can be made from other materials. One example of how luer cone 60 and channel 64 can be configured for complementary mating is disclosed in International Standard ISO 549/1-1986(E) which is incorporated herein by specific reference. Similarly, one example of how first threads 36, 38 and engagement threads 58 can be configured for threaded engagement is disclosed in International Standard ISO 594-2:1991 (E) which was previously incorporated herein by specific reference. Further disclosure with regard to the configuration and coupling of the syringes and mixing of components between the two syringes is disclosed in U.S. patent application Ser. No. 09/251,887, filed Feb. 19, 1999 which is incorporated herein by specific reference.

Depicted in FIG. 4 is a second syringe 64 that can also be used for coupling with first syringe 12. Second syringe 64 is substantially identical to second syringe 14 except that lure cone 60 has been removed. Like elements between syringes 14 and 64 are identified by like reference characters.

The present invention also includes means mounted on exterior surface 30 of tubular tip 22 at a location longitudinally spaced apart from first threads 36, 38 for frictionally engaging second syringe 14, 64 when first syringe 12 is threadedly coupled to second syringe 14, 64. By way of example and not by limitations, depicted in FIGS. 1, 2, 5, and 6 are a pair of spaced apart second threads 66, 68 projecting from exterior surface 30 of tubular tip 22. Second threads 66, 68 are spaced longitudinally apart from first threads 36, 38 and are configured to at least partially encircle tubular tip 22. In one embodiment, second threads 66, 68 are substantially identical to first threads 36, 38.

Second threads 66, 68 also have opposing tapered side walls 82 and 84 which bound a pair of second thread grooves 86, 88. A central longitudinal axis 90 extends through second thread grooves 86 and 88. Second threads 66, 68 can have the same alternative configurations as discussed above with regard to first threads 36, 38. In the embodiment depicted in FIG. 6, first thread groove 76 and second thread groove 86 are aligned such that central longitudinal axis 80 and central longitudinal axis 90 are aligned. Thread grooves 78 and 88 are similarly aligned. As such, when first syringe 12 is threadedly coupled with second syringe 14, engagement threads 58 of second syringe 14 are threadedly received in both the first thread grooves 76, 78 and the second thread grooves 86, 88. The frictional engagement of the second threads 66, 68 with second syringe 14 facilitates a tighter coupling between syringes 12 and 14, thereby preventing leaking or accidental uncoupling as components are passed between the syringes.

It is noted that although first threads 36, 38 and second threads 66, 68 may in one embodiment have the same configuration, the fact that first threads 36, 38 and second threads 66, 68 are longitudinally spaced apart, as opposed to being integral, provides unexpected and surprising results. Specifically, injection molding a syringe, such as first syringe 12, wherein a thread is formed on tip 22 that continuously encircles tip 22 two or more times requires that the thread be undercut at one end so as to enable release of the mold from the part. This irregular thread configuration results in irregular and loose fitting of the two syringes. In contrast, by forming two longitudinally spaced apart threads, as in the present invention, the two sets of threads can be injection molded each having the same exacting tolerances, thereby providing a tighter fit between the two syringes.

Depicted in FIGS. 7–10 are alternative embodiments of the means for frictionally engaging which are illustrated in views similar to FIG. 6. In the embodiment depicted in FIG. 7, first threads 36 and 38 are positioned as previously discussed with regard to FIG. 6. Second threads 66 and 68 also have the same configuration as discussed with regard to FIG. 6. In the embodiment depicted in FIG. 7, however, second threads 66, 68 are horizontally shifted relative to second threads 66, 68 in FIG. 6. As such, central longitudinal axis 80 for first thread groove 78 and central longitudinal axis 90 for second thread groove 88 are offset a defined amount as opposed to being aligned. As a result, engagement threads 58 of second syringe 14 couple normally with first threads 36, 38. As engagement threads 58 enter second thread grooves 86, 88, engagement threads 58 are not centrally disposed within grooves 86, 88 but rather are biased hard against one of the side walls 82, 84 of second threads 66, 68. This biased contact increases frictional engagement between engagement threads 58 and second threads 66, 68, thereby increasing the seal and coupling strength between syringes 12 and 14.

Figure 8:
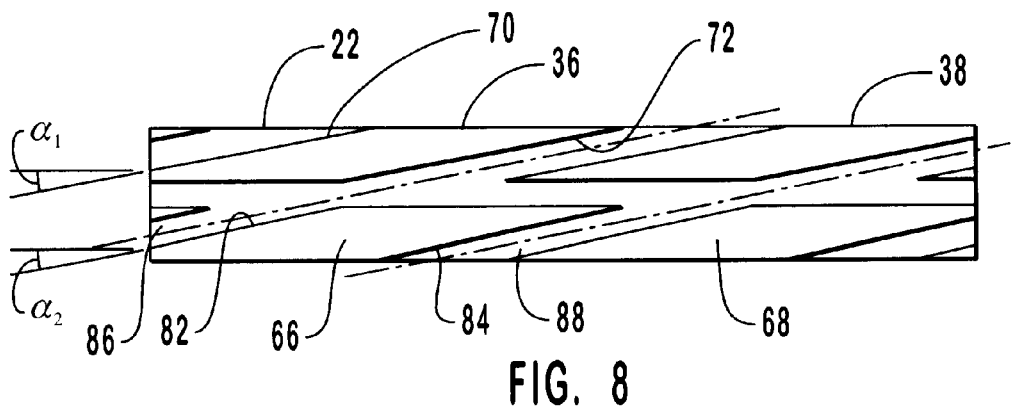
FIG. 8 is a top plan view of an alternative embodiment of the thread assembly shown in FIG. 6 wherein the second threads are positioned at a pitch different than the first threads.

Depicted in FIG. 8, first threads 36, 38 are substantially identical to those previously discussed with regard to FIG. 6. In this configuration, side walls 70 and 72 of first threads 36, 38 are pitched at an angle $\alpha_1$ relative to a horizontal plane which can be any desired angle. Second threads 66, 68 are also substantially identical to those previously discussed with regard to FIG. 6. In the embodiment of FIG. 8, however, side walls 82 and 84 of second threads 66, 68 are disposed at a pitch $\alpha_2$ relative to the horizontal wherein $\alpha_2$ is greater than $\alpha_1$. The pitch of second threads 66, 68 is thus different than the pitch of first threads 36, 38.

As a result of the variance in pitch, engagement threads 58 couple normally with first threads 36, 38 but increasingly bias against second threads 66, 68 as engagement threads 58 are threaded into second thread grooves 86, 88. The increased frictional engagement increases the seal and coupling strength between syringes 12 and 14. In an alternative embodiment, $\alpha_2$ can also be smaller than $\alpha_1$ and still achieve the same effect.

Figure 9:
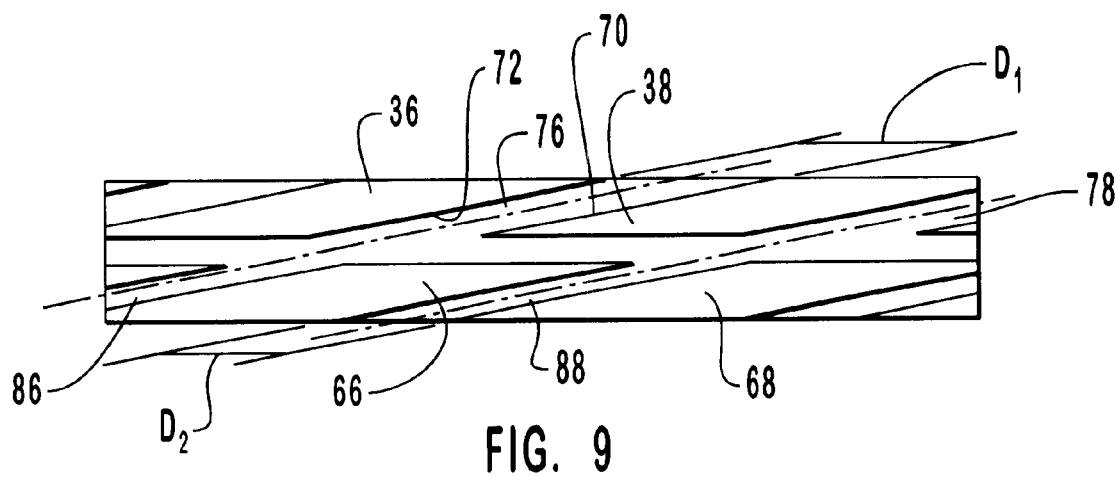
FIG. 9 is a top plan view of an alternative embodiment of the thread assembly shown in FIG. 6 wherein the second threads bound a groove that is smaller than the groove of the first threads.

Depicted in FIG. 9, first threads 36, 38 and second threads 66, 68 are again substantially identical to those disclosed in FIG. 6. In FIG. 9, however, first threads 36, 38 are separated by a maximum distance $D_1$ which is the maximum width of first thread grooves 76, 78. This maximum separation distance $D_1$ is constant along the length of side walls 70, 72 of first threads 36, 38. In contrast, second threads 66, 68 are separated by a constant maximum distance $D_2$ that is smaller than distance $D_1$. As a result of second thread grooves 86, 88 being narrower than first thread grooves 76, 78, engagement threads 58 have a tighter frictional engagement with second threads 66 and 68, thereby increasing the seal and coupling strength between syringes 12 and 14.

Figure 10:
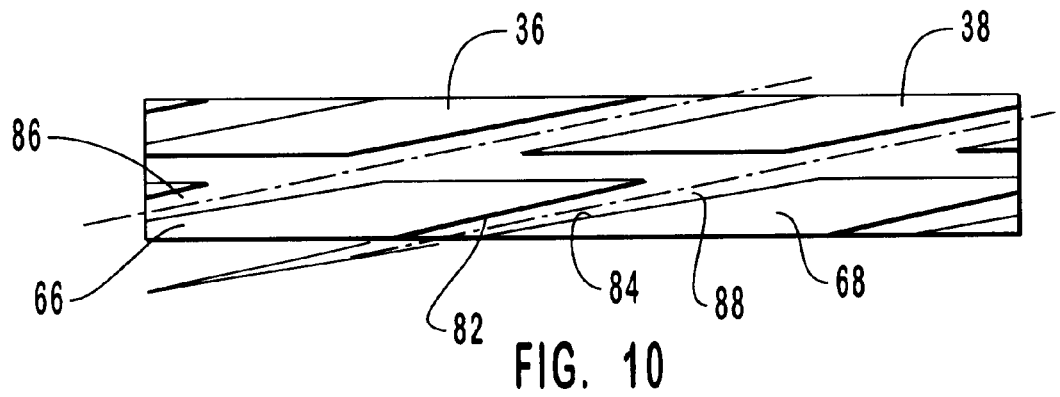
FIG. 10 is a top plan view of an alternative embodiment of the thread assembly shown in FIG. 6 wherein the second threads bound a groove that is tapered.

Depicted in FIG. 10, first threads 36, 38 and second threads 66, 68 are again substantially identical to those disclosed with regard to FIG. 6. In FIG. 10, however, second threads 66, 68 are configured such that the distance between opposing facing side walls 82 and 84 varies in width. More specifically, side walls 82 and 84 constrict in a wedge shape configuration such that engagement threads 58 are wedged between second threads 66, 68 when engagement threads 58 are received within second thread grooves 86, 88. This wedging of engagement threads 58 increases the seal and coupling strength between syringes 12 and 14.

Figure 11:
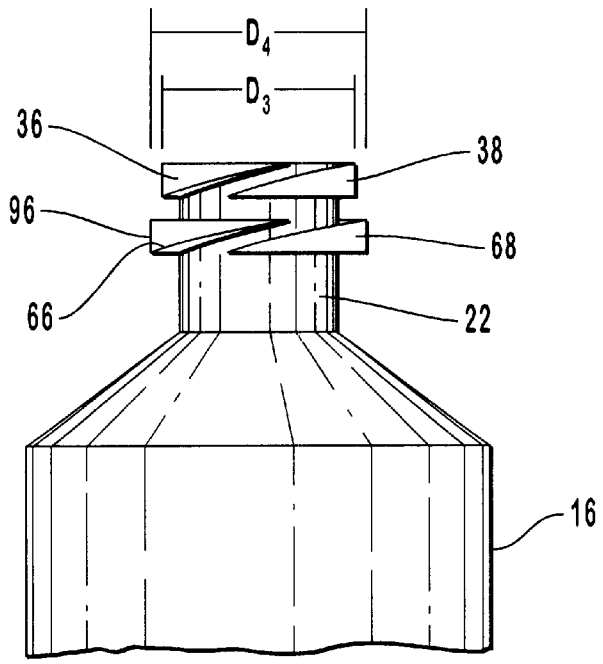
FIG. 11 is an elevated side view of the tip of the first syringe shown in FIG. 1 wherein the second threads have a maximum outer diameter greater than the maximum outer diameter of the first threads.
Figure 12:
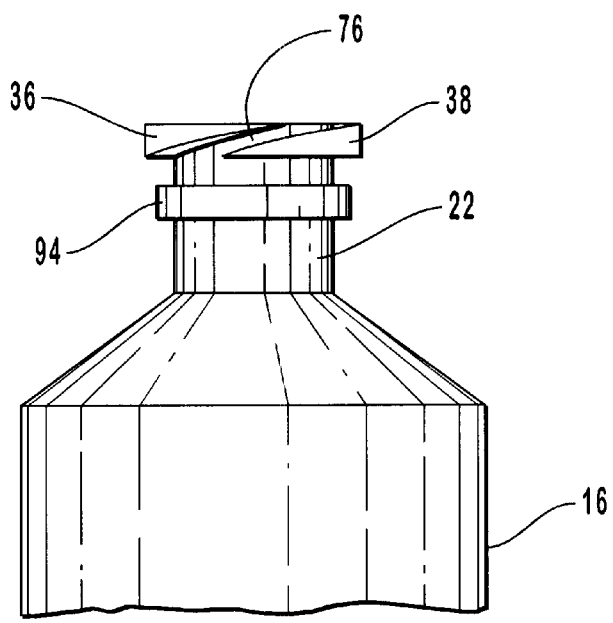
FIG. 12 is an elevated side view of an alternative embodiment of the first syringe shown in Figure wherein the second threads are replaced by and an annular ridge.
Figure 13:
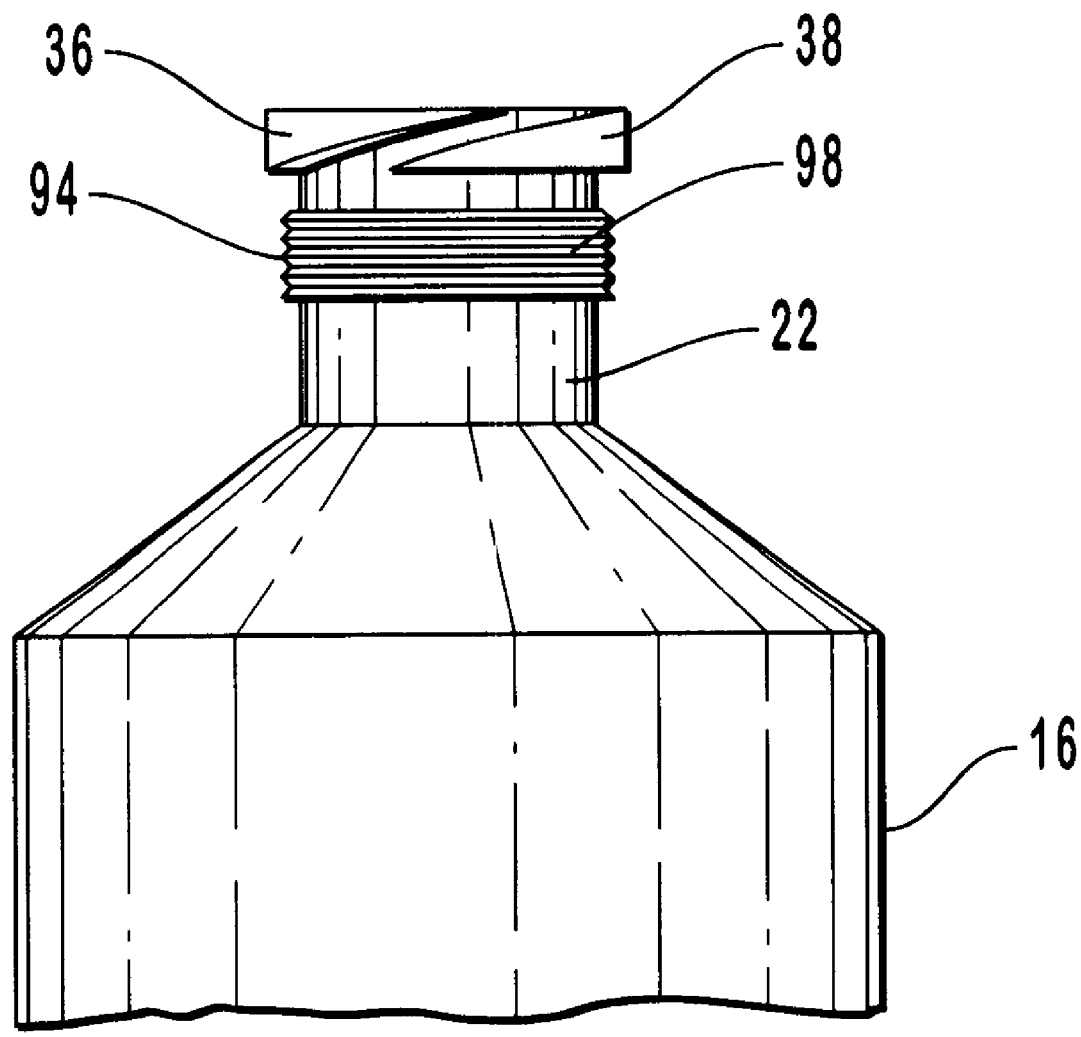
FIG. 13 is an elevated side view of an alternative embodiment of the first syringe shown in FIG. 12 wherein a plurality of smaller ridges are formed on the annular ridge.

Depicted in FIGS. 11–13 are yet other embodiments of the means for frictionally engaging against second syringe 12. As depicted in FIG. 11, first threads 36, 38 have a maximum outer diameter $D_3$. Second threads 66 and 68 have a maximum outer diameter $D_4$. Outer diameter $D_4$ is larger than diameter $D_3$ such that as tip 22 is received within collar 48 (FIGS. 3 and 4), second threads 66, 68 bias in greater frictional engagement against interior surface 56 of collar 48. Second threads 66, 68 have a have an exposed top surface 96 that can be either flat, as depicted, or sloped so as to wedge against interior surface 56 of collar 48.

In the embodiment depicted in FIG. 11, diameter $D_4$ is greater than the diameter $D_3$ as a result of second threads 66, 68 having a greater thickness than first threads 36, 38. In an alternative embodiment, first threads 36, 38 and second threads 66, 68 can have the same thickness and yet still have a variance in maximum diameter as a result of varying the diameter of tip 22 along the length thereof.

Depicted in FIG. 12, first threads 36, 38 are disposed on tip 22 as previously discussed with regard to FIG. 11. Second threads 66, 68, however, have been replaced by a ridge 94 that radially outwardly projects from tip 22 so as to encircle tip 22. Ridge 94 is configured such that engagement threads 58 of syringe 12 (FIGS. 3 and 4) pass through first thread grooves 76, 78 and then bias into direct contact with ridge 94. As a result, engagement threads 58 either ride over and/or gouge into ridge 94 so as to create a tight frictional engagement between engagement threads 58 and ridge 94. In alternative embodiments, ridge 94 need not completely encircle tip 22. Rather, one or more shorter ridges that only partially encircle tip 22 may project from tip 22 in alignment with one or more of first thread grooves 76, 78.

Depicted in FIG. 13, ridge 94 has a plurality of smaller ridges 98 or teeth formed on a top surface thereof. Smaller ridges 98 act to bite against engagement threads 58 so as to further retain syringes 12 and 14 in locked frictional engagement.

It is appreciated that second threads 66, 68 and ridge 94 can be designed having a variety of other sizes and shapes and that they can be placed in a variety of different orientations and positions and still achieve the desired effect of increasing frictional engagement with second syringe 14. For example, it is appreciated that the first threads and the second threads can each comprise one thread or three or more threads. It is also appreciated that the above embodiments and alternatives thereof can be grouped in different combinations to achieve the desired effect. Furthermore, the inventive thread assemblies as disclosed herein can be used on other structures besides syringes. For example, the thread assemblies can be used on discrete connectors for coupling syringes, cartridges, and other types of containers which are desired to couple together.

Finally, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A thread structure comprising:
   a tubular member having an interior surface and an exterior surface, the tubular member having a longitudinal axis extending therethrough;
   a pair of spaced apart first threads projecting from the exterior surface of the tubular member so as to at least partially encircle the tubular member; and
   a pair of spaced apart second threads projecting from the exterior surface of the tubular member so as to at least partially encircle the tubular member, the second threads being spaced longitudinally apart from the first threads.

2. A thread structure as recited in claim 1, wherein
   at least a portion of each of the first threads is disposed in a first plane perpendicular to the longitudinal axis of the tubular member; and
   at least a portion of each of the second threads is disposed in a second plane perpendicular to the longitudinal axis of the tubular member.

3. A thread structure as recited in claim 1, wherein the first threads comprise double right hand threads.

4. A thread structure as recited in claim 1, wherein
   the first threads have a maximum outer diameter; and
   the second threads have a maximum outer diameter, the maximum outer diameter of the second threads being greater than the maximum outer diameter of the first threads.

5. A thread structure as recited in claim 1, wherein
   the first threads have a maximum thickness; and
   the second threads have a maximum thickness, the maximum thickness of the second threads being greater than the maximum thickness of the first threads.

6. A thread structure as recited in claim 1, wherein
   the first threads bound a first thread groove therebetween, the first thread groove having a first central axis longitudinally extending therethrough; and
   the second threads bound a second thread groove therebetween, the second thread groove having a second central axis longitudinally extending therethrough, the first thread groove and the second thread groove being aligned so that the first and second central axes are aligned.

7. A thread structure as recited in claim 1, wherein
   the first threads bound a first thread groove therebetween, the first thread groove having a first central axis longitudinally extending therethrough; and
   the second threads bound a second thread groove therebetween, the second thread groove having a second central axis longitudinally extending therethrough, the first thread groove and the second thread groove being offset so that the first and second central axes are offset.

8. A thread structure as recited in claim 1, wherein
   the first threads are oriented at a first pitch; and
   the second threads are oriented at a second pitch that is different than the first pitch.

9. A thread structure as recited in claim 1, wherein
   the first threads bound a first thread groove therebetween, the first thread groove having a substantially constant maximum width along its length; and the second threads bound a second thread groove therebetween, the second thread groove having a substantially constant maximum width along its length, the maximum width of the second thread groove being smaller than the maximum width of the first thread groove.

10. A thread structure as recited in claim 1, wherein the second threads bound a thread groove therebetween, the thread groove having a maximum width that varies along the length of the thread groove.

11. A thread structure as recited in claim 1, wherein the tubular member comprises a portion of a syringe barrel.

12. A thread structure adapted for coupling two syringes together to facilitate the transfer of material between the syringes in a secure and essentially liquid tight fashion, comprising:

a tubular member having an interior surface and an exterior surface, the tubular member having a longitudinal axis extending therethrough, said tubular member serving as an outlet tip for one of the two syringes;

a pair of spaced apart threads outwardly projecting from the exterior surface of the tubular member so as to at least partially encircle the tubular member, at least a portion of each of the threads being disposed in a plane perpendicular to the longitudinal axis of the tubular member, the threads bounding a thread groove; and a ridge outwardly projecting from the exterior surface of the tubular member, the ridge being aligned with the thread groove.

13. A thread structure as recited in claim 12, wherein each of the threads only partially encircles the tubular member.

14. A thread structure as recited in claim 12, wherein the ridge is longitudinally spaced apart from the threads.

15. A thread structure as recited in claim 12, wherein the ridge completely encircles the tubular member.

16. A thread structure as recited in claim 12, wherein the ridge has a top surface with a plurality of ridges formed thereon.

17. A thread structure as recited in claim 12, wherein the ridge only partially encircles the tubular member.

18. A thread structure comprising:

a tubular member having an interior surface and an exterior surface, the tubular member having a longitudinal axis extending therethrough;

a pair of spaced apart threads outwardly projecting from the exterior surface of the tubular member so as to at least partially encircle the tubular member, at least a portion of each of the threads being disposed in a plane perpendicular to the longitudinal axis of the tubular member, the threads bounding a thread groove; and a plurality of ridges outwardly projecting from the exterior surface of the tubular member and being longitudinally spaced apart from the threads.

19. A thread structure as recited in claim 18, wherein the ridges are aligned with the thread groove.

20. A thread structure as recited in claim 18, wherein at least some of the ridges completely encircle the tubular member.

21. A thread structure as recited in claim 18, wherein at least some of the ridges only partially encircle the tubular member.

22. A thread structure as recited in claim 1, wherein the thread structure is adapted for coupling two syringes together to facilitate the transfer of material between the syringes in a secure and liquid tight fashion.

23. A thread structure as recited in claim 18, wherein the thread structure is adapted for coupling two syringes together to facilitate the transfer of material between the syringes in a secure and liquid tight fashion.

* * * * *